(12) United States Patent
Leflour (10) Patent No.: US 9,151,720 B2
(45) Date of Patent: Oct. 6, 2015

(54) DEVICE FOR TESTING A SURFACE INCLUDING AN EXTRACTION UNIT FOR EXTRACTING A SHIFTED FREQUENCY COMPONENT AND ASSOCIATED METHOD

(71) Applicant: DASSAULT AVIATION, Paris (FR)

(72) Inventor: Gerard Leflour, Paris (FR)

(73) Assignee: DASSAULT AVIATION, Paris (FR)

( * ) Notice: Subject to any disclaimer, the term of this patent is extended or adjusted under 35 U.S.C. 154(b) by 149 days.

(21) Appl. No.: 13/691,354

(22) Filed: Nov. 30, 2012

(65) Prior Publication Data

US 2013/0154668 A1 Jun. 20, 2013
US 2014/0002107 A9 Jan. 2, 2014

(30) Foreign Application Priority Data

Dec. 2, 2011 (FR) ...................................... 11 03695

(51) Int. Cl.
   *G01R 27/32* (2006.01)
   *G01N 22/00* (2006.01)
   *G01N 22/02* (2006.01)

(52) U.S. Cl.
   CPC ................ *G01N 22/00* (2013.01); *G01N 22/02* (2013.01); *G01R 27/32* (2013.01)

(58) Field of Classification Search
   CPC . G01N 22/02; G01N 2223/611; G01N 22/00; G01N 23/223; G01N 27/04; G01N 2035/00782; G01N 23/22; G01N 23/2251; G01N 31/223; G01N 35/00732; G01N 35/00871; G01B 11/2513; G01R 33/341; G01R 33/3635; G01R 33/365; G01R 33/3685; G01R 33/5659; G06F 2221/2111; H04B 7/1555; H04B 7/15564; G01F 23/2962
   See application file for complete search history.

(56) References Cited

U.S. PATENT DOCUMENTS

| 2,999,982 | A | | 9/1961 | Broussaud |
| 3,490,037 | A | * | 1/1970 | Williams ...................... 324/644 |
| 4,123,703 | A | | 10/1978 | Robinson |
| 4,818,930 | A | * | 4/1989 | Flemming et al. ............ 324/631 |
| 5,075,863 | A | * | 12/1991 | Nagamune et al. ........... 702/159 |
| 5,384,543 | A | | 1/1995 | Bible et al. |
| 5,859,535 | A | * | 1/1999 | Liu ............................... 324/632 |
| 2002/0011947 | A1 | | 1/2002 | Stolarczyk et al. |
| 2003/0132760 | A1 | | 7/2003 | Bray et al. |

FOREIGN PATENT DOCUMENTS

WO      2004/074823      9/2004

OTHER PUBLICATIONS

French Search Report filed in French Application No. 1103695 dated Jun. 29, 2012.

* cited by examiner

*Primary Examiner* — Vinh Nguyen
(74) *Attorney, Agent, or Firm* — Davidson, Davidson & Kappel, LLC (57) ABSTRACT

A device including a holder and a transmitter supported by the holder is provided. The transmitter is capable of transmitting an electromagnetic signal toward the surface any transmission frequency (Fe). The device also includes a receiver for receiving a signal reflected on the surface. The device also includes a guide assembly for guiding the movement of the holder to move the transmitter and the receiver across from the surface, tangentially relative to the surface. The device also includes an extraction unit for extracting, in the signal received by the receiver, a shifted frequency component of the transmission frequency resulting from a local impedance variation of the surface. The extraction unit produces an extracted signal representative of the state of the surface from the shifted frequency component.

16 Claims, 4 Drawing Sheets

DEVICE FOR TESTING A SURFACE INCLUDING AN EXTRACTION UNIT FOR EXTRACTING A SHIFTED FREQUENCY COMPONENT AND ASSOCIATED METHOD

CROSS-REFERENCE TO RELATED APPLICATIONS

This application claims benefit of French Patent Application No. 1103695, filed Dec. 2, 2011, which is herein incorporated by reference.

BACKGROUND OF THE INVENTION

1. Field of the Invention

The present invention relates to a device for testing a surface, comprising a holder; a transmitter supported by the holder, the transmitter being able to transmit an electromagnetic signal to the surface at a transmission frequency; a receiver for receiving a signal reflected on the surface. Such a device is intended to test the heterogeneity and/or local defects that may be present on surfaces.

In particular, such a device is designed to determine the radioelectric homogeneity of the surface, by determining the variations in the radioelectric properties of the surface using a non-destructive test method.

2. Description of the Related Art

Good radioelectric surface homogeneity may be required in many applications, in particular those designed to produce and incorporate antennas, in the insulation of equipment sensitive to strong fields, and in reducing the diffusion of waves lighting those surfaces.

In particular, the parabolic reflectors used in certain high-gain antennas must have a homogenous surface conductivity. Without such homogeneity, the conductivity defects cause dispersions of the electromagnetic radiation that increase the standing wave levels and amplify the interactions between adjacent systems.

The radomes present across from the antennas must on the contrary be radioelectrically transparent. Transparency discontinuities decrease the intensity of the signals transmitted and received and diffuse the waves outside the angular sectors of interest.

Furthermore, in the case where part of the antenna system must be isolated, an absorbent material may be used to cover the antenna system. It is then necessary for the surface reflectivity to be homogenous.

To detect radioelectric surface defects, it is known to examine the variations of the radioelectric properties of the surfaces.

In that context, non-destructive techniques are used. Among these techniques, it is known to use Foucault currents using a coil by creating a magnetic field near the surface penetrating the material. This penetration creates induced currents that are picked up by the coil or measured by an adjacent coil.

The induced currents result from the conductivity and magnetic permeability of the material and influence the impedance specific to the coil or the mutual impedance between two coils of the device.

In certain cases, to improve the measuring quality, it is known to perform localized electromagnetic reflectivity measurements. These measurements may be done using an antenna and a reflector, or using a waveguide.

Radar techniques may also be used by moving a pair of transmission and receiving antennas relative to a scene to obtain a spatial resolution along the movement axis.

However, the existing techniques have many limitations. Thus, the technique using Foucault currents only makes it possible to test conductive or magnetic surfaces. Furthermore, for frequencies above 300 MHz, the coils used as sensors generate spatial radiation and become sensitive to echoes outside the area of interest.

Local electromagnetic reflectivity measurements are limited in terms of resolution, in particular in light of the width of the lighting area, which is typically in the vicinity of a half-wavelength. These measuring methods are therefore not suited to detecting localized impedance discontinuities, for example resulting from a slit related to a crack in a metallization layer.

Radar techniques are expensive and sometimes difficult to carry out, in particular to avoid outside echoes that saturate the measurement. It is generally necessary to perform the measurements in an anechoic enclosure.

Furthermore, to obtain a good spatial resolution on the detection of the defects, the measuring frequency band must be wide, which leads to significant measuring times.

SUMMARY OF THE INVENTION

One aim of the invention is therefore to obtain a non-destructive measuring device for radio electric surface property defects, the measurement being very sensitive to the detected defects, but not particularly sensitive to the outside environment, the method being usable over a wide frequency range, while being simple to carry out.

To that end, the invention relates to a device of the aforementioned type, characterized in that the device comprises a guide assembly for the holder to move the transmitter and the receiver across from the surface, tangentially relative to the surface, the device comprising an extraction unit for extracting a shifted frequency component of the transmission frequency resulting from a local impedance variation of the surface in the signal received by the receiver, the extraction unit producing an extracted signal that is representative of a state of the surface from the shifted frequency component.

The device according to the invention may include one or more of the following features, considered alone or according to any technically possible combinations.

The shifted frequency component is representative of a Doppler shift between the transmission frequency and the reception frequency at a speed of travel of the device on the surface.

The extraction unit comprises a mixer for mixing at least part of the signal received by the receiver with at least part of the transmission signal transmitted by the transmitter and a nonlinear component capable of producing a processed signal comprising an oscillation at the shifted frequency component based on the combined signal obtained in the mixer.

It comprises a frequency filter capable of eliminating the frequencies below a minimum cutoff frequency, advantageously equal to $2 V_{min} F_e/c$, where $V_{min}$ is a lower bound of the speed of movement of the device on the surface, $F_e$ is the transmission frequency, and c is the speed of the electromagnetic radiation in the vacuum, the frequency filter being capable of eliminating frequencies above an upper cutoff frequency, in particular equal to $2 V_{max} F_e/c$ where $V_{max}$ is an upper bound of the speed of movement of the device on the surface.

It comprises a display unit capable of displaying a variable intensity signal as a function of the state of the surface, the variable intensity signal being produced from the signal extracted in the extraction unit.

The display unit comprises a processing assembly for processing the extracted signal obtained as output from the extraction unit, the processing assembly comprising an enclosure detector advantageously comprising a rectifier and an integrator.

It comprises an analog-digital converter capable of digitizing the extracted signal from the extraction unit.

It comprises a detection sensor for detecting the position of the device on the surface, the device advantageously comprising an assembly for storing the extracted signal obtained by the extraction unit as a function of the position of the device on the surface.

Said holder is portable to be grasped in a user's hand.

The holder comprises a conductive wall delimiting a cavity, the transmitter and the receiver being received in the cavity.

The conductive wall delimits a lower opening through which the cavity opens, the lower opening being intended to be positioned across from the surface.

The shifted frequency component is representative of a Doppler shift between the transmission frequency and the reception frequency produced by a speed of travel of the device on the surface, and/or by a speed of appearance of a surface defect across the lower opening, the speed of appearance following a travel of the device.

The holder comprises at least one shield made from a material absorbing the electromagnetic waves at the transmission frequency, the shield being positioned in the cavity delimited by the conductive wall, across from the transmitter and the receiver.

The guide assembly comprises at least one skid and/or a rolling member capable of keeping the transmitter and the receiver at a substantially constant distance across from the surface, during the tangential movement of the holder on the surface.

The guide assembly comprises a guide mechanism driven from the holder across from the surface, advantageously keeping the device separated from the surface.

It comprises a computation assembly for computing an equivalent radar surface, based on the signal extracted by the extraction unit.

The invention also relates to a method for testing a surface, characterized in that it comprises the following steps:

Providing a device as described above;

Tangential movement of the holder across from the surface by means of the guide assembly;

Transmission of an electromagnetic signal at a transmission frequency by the transmitter;

Reception of a reflected signal on the surface by the receiver;

Extraction, by the extraction unit, of a shifted frequency component of the transmission frequency in the signal received by the receiver, the shifted frequency component resulting from a local impedance variation of the surface;

Production of an extracted signal representative of a state of the surface from the extracted frequency component.

The method according to the invention may comprise one or more of the following features, considered alone or according to any technically possible combinations.

The extraction step comprises mixing at least part of the reception signal received by the receiver with at least part of the transmission signal transmitted by the transmitter to form a combined signal, and the application of the combined signal to a nonlinear component to produce an oscillating extracted signal at the shifted frequency component.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 1:
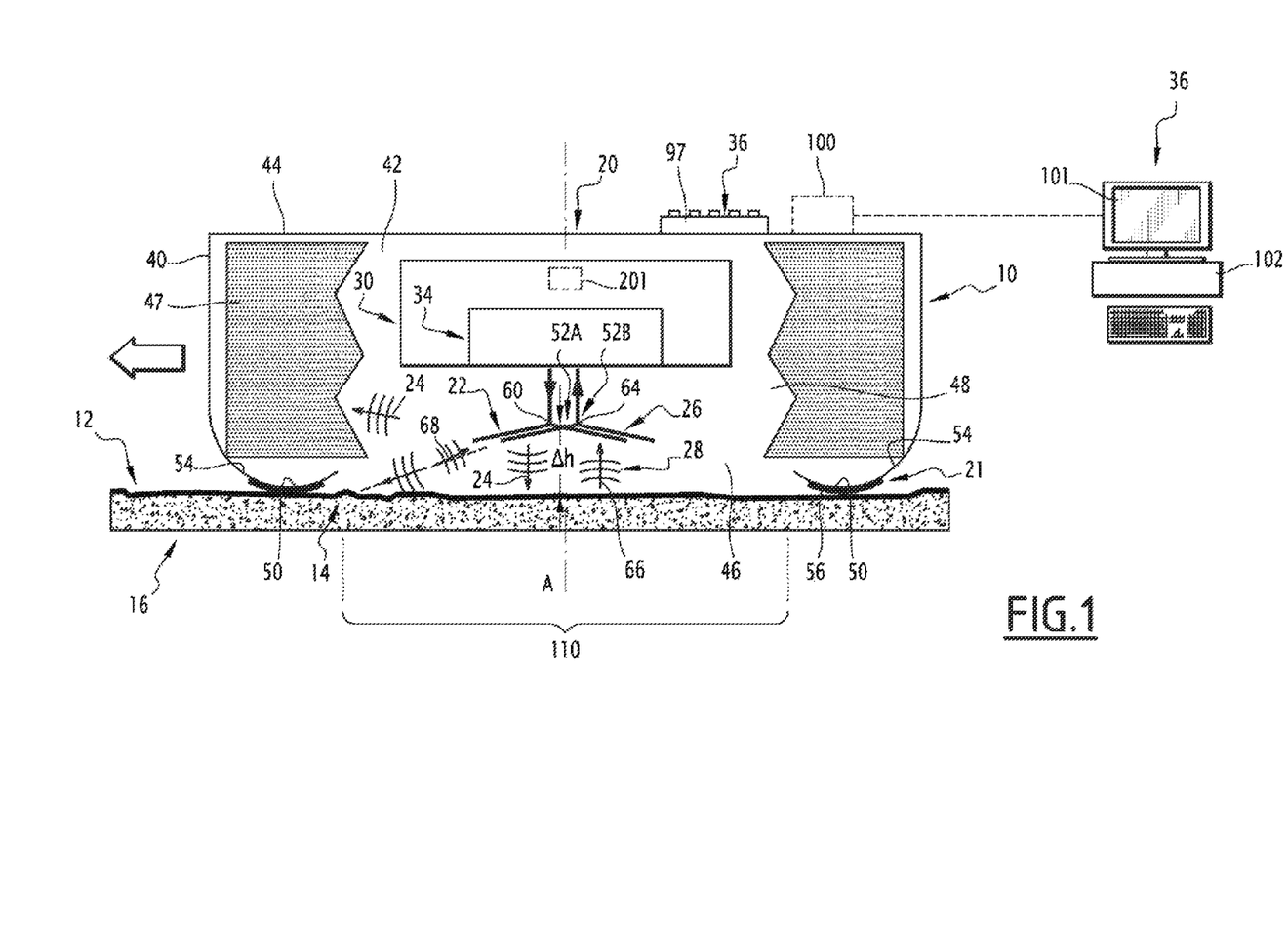
FIG. 1 is a diagrammatic partial cross-sectional view of a tester according to the invention for testing a surface.
Figure 2:
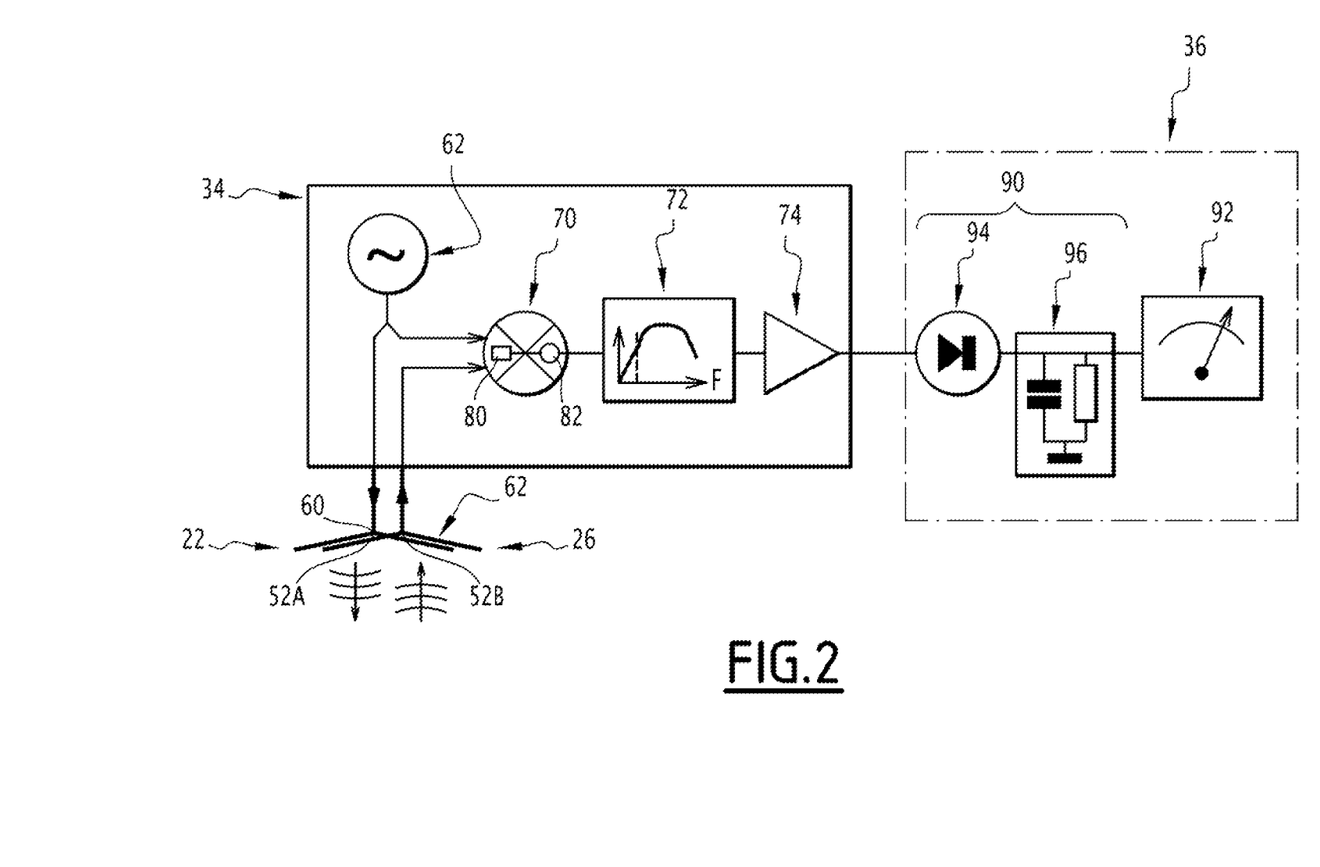
FIG. 2 is a diagrammatic view of the processing assembly for processing the signal received by the device of FIG. 1.
Figure 3:
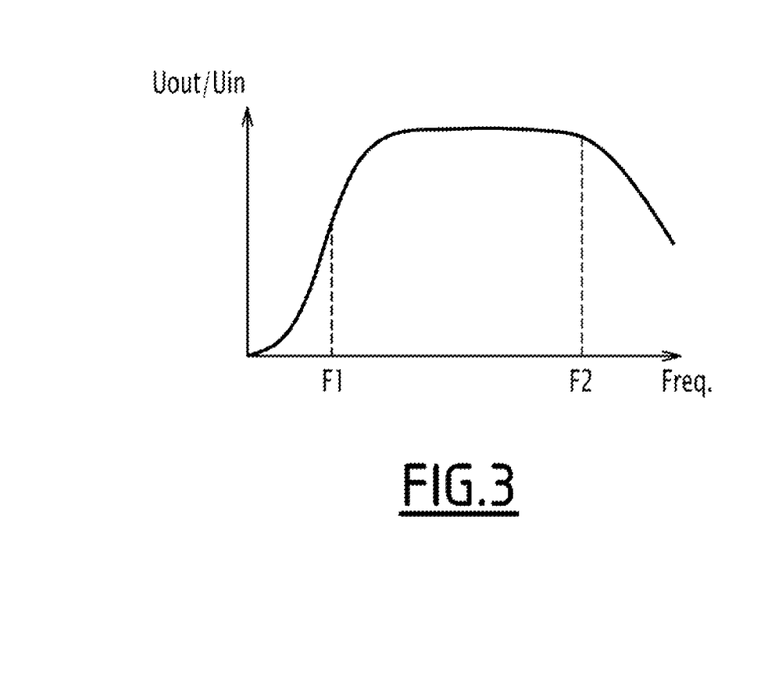
FIG. 3 illustrates the frequency behavior of a filter used in the processing assembly of FIG. 2.

A first device 10 for testing a surface 12 according to the invention is illustrated by FIGS. 1 and 2.

This device 10 is designed to detect uniformity defects in the impedance of the surface 12 by relative movement in relation to the surface 12.

In this example, the device 10 is a portable device, which may be moved by a user's hand or by a robotic arm.

The surface 12 is a substantially radioelectrically homogenous surface, which has periodic defects 14. These periodic defects 14 may be detected using the device 10 according to the invention.

The surface 12 is for example a conductive surface, such as a metal surface formed in the mass of a part 16, or forming a coating of the part 16. Alternatively, the surface 12 is insulating. It is for example formed with a base of a dielectric material.

The part 16, the surface state of which is tested, is for example a parabolic reflector used in an antenna, or a radome designed to be mounted on a stationary facility or on a moving platform such as an aircraft.

Alternatively, the part 16 is a coating part for a radioelectric measuring means, such as a radar, or a conductive wall designed to separate a high electromagnetic radiation generator from equipment sensitive to radiation by the Faraday cage effect.

The device 10 detects low impedance variations of the surface 12.

The impedance of a surface characterizes the response thereof to an electromagnetic wave.

Hereafter, the impedance is defined relative to the electric and magnetic fields of the interface between the surface and the outer medium. The fields are described by an amplitude and a phase according to their polarization direction.

The impedance is calculated using a complex value for a given frequency. The reflection coefficient R of an electromagnetic wave establishes the intensity ratio between a reflected planar wave and an incident planar wave.

The coefficient R is deduced from the average impedance Z of the surface using the relationship:

$$R = \frac{Z-1}{Z+1}. \tag{1}$$

The impedance Z is defined at all points of the surface 12. Its average value characterizes the specular reflection of a wave and its fluctuations characterizing the diffuse reflection.

The device 10 is designed to measure the local discontinuities of the surface impedance Z sensitively, so as to detect local defects 14 on that surface.

Through this test of the uniformity of the surface impedance, it is possible to localize defects indirectly that affect other properties of interest, such as the mechanical properties, the thicknesses of any protective layer, resistance to wear and corrosion, etc.

In reference to FIG. 1, the device 10 according to the invention comprises a moving holder 20 and a guide assembly 21 for guiding the movement of the moving holder 20 tangentially relative to the surface 12 to allow scanning of the surface 12 at the tangential speed of movement V.

The device 10 also comprises a transmitter 22 capable of creating an electromagnetic signal 24 designed to be oriented toward the surface 12 and a receiver 26 for detecting a signal 28 reflected by the surface 12 from the transmission signal 24.

The transmitter 22 and the receiver 26 are supported by the holder 20 and are jointly movable therewith.

The device 10 also comprises a control unit 30 for controlling the transmitter 22 and the receiver 26, and an extraction unit 34 for extracting an extracted signal representative of a local impedance variation of the surface in the signal received by the receiver 26.

In this example, the device 10 also comprises a unit 36 for processing and displaying the extracted signal representative of the local impedance variation of the surface.

The holder 20 is made up of a hollow housing 40 delimiting an inner cavity 42 for receiving the transmitter 22 and the receiver 26.

The housing 40 comprises a hollow metal wall 44 delimiting the cavity 42. The metal wall 44 delimits the cavity 42 upward away from the surface 12, and at the periphery of the cavity 42, around the transmitter 22, the receiver 26, and the central unit 30.

The metal wall 44 delimits a lower opening 46 through which the cavity 42 opens. The lower opening 46 is designed to be positioned across from the surface 12 to be tested.

Advantageously, the holder 20 comprises an absorbent shield 47 positioned on the wall 44 in the cavity 42. The shield 47 extends at the periphery of the cavity 42, around the transmitter 22 and the receiver 26. It is for example made up of a ring of a material absorbing the electromagnetic waves of the transmission frequency of the receiver 22. This absorbent material is for example a foam containing carbon particles or a silicone or urethane matrix filled with magnetic particles. Such materials are marketed by the companies Emerson and Cuming Microwave Products under the brand Eccosorb.

The shield 47 inwardly delimits a central passage 48. The computation unit 30 and the processing unit 34, the transmitter 22 and the receiver 26 are positioned in the central passage 48.

In the example shown in FIG. 1, the guide assembly 21 of the holder 20 on the surface 12 comprises contact members 50 with the surface 12 protruding from the holder 20.

The contact members 50 can keep the support 20, the transmitter 22, and the receiver 26 substantially locally parallel relative to the surface 12, at a small and predetermined distance with respect to the surface 12.

In this way, the transmitter 22 and the receiver 26 can be moved tangentially relative to the surface 12 to scan and detect periodic defects while keeping the distance separating the transmitter 22 and the receiver 26 from the surface 12 substantially constant.

The bearing members 50 are configured to keep the transmitter 22 and the receiver 26, and in particular their phase centers 52A, 52B that define the origin of the capture of the radiation, at a distance from the surface 12 comprised between 0.1 times and 1 time the transmission wavelength $\lambda_e$ of the radiation transmitted by the transmitter 22, advantageously a distance comprised between 0.2 times and 0.5 times the transmission wavelength $\lambda_e$.

In particular, the height difference denoted $\Delta h$ in FIG. 1 between the respective phase centers 52A, 52B of the transmitter 22 and the receiver 26 and the plane P defined by the points of the members 50 vertically furthest from the centers 52A, 52B on the members 50 is comprised between 0.1 times and 1 time the transmission wavelength $\lambda_e$ of the radiation transmitted by the transmitter 22, in particular between 0.2 times and 0.5 times the transmission wavelength $\lambda_e$.

For the usual transmission frequencies used by the device 10, this height difference $\Delta h$ is for example comprised between 6 mm and 1.5 mm.

In the example shown in FIG. 1, the contact members 50 are formed by skids 54, which protrude downward from the metallic wall 44.

The skids 54 have a lower contact surface 56 with the surface 12 that is designed to slide on the surface 12. The inner surface 56 is for example provided with an anti-adhesive coating.

As specified above, the transmitter 22 is positioned in the cavity 42 delimited by the holder 20. It is advantageously positioned in the vicinity of a central axis A-A' of the cavity 42.

The transmitter 22 comprises a transmission antenna 60 capable of transmitting a transmission signal formed from electromagnetic radiation at a frequency $F_e$ comprised between 100 MHz and 1000 GHz. More generally, the signal may have a transmission frequency $F_e$ of more than 1000 GHz.

The transmission antenna 60 transmits the signal 24 in all directions, and in particular directly toward the surface 12, in a grazing manner toward the surface 12, and toward the metal wall 44 of the holder 20.

The antenna 60 is for example made up of one or more radiation elements. The antenna 60 is advantageously compact with a size smaller than a half-wavelength and may have a very small bandwidth around the frequency $F_e$.

In one particular embodiment, the antenna 60 is an antenna patch.

The transmitter 22 also comprises an oscillator 62 (visible in FIG. 2) capable of creating the transmission signal periodically at a transmission frequency $F_e$.

The oscillator 62 is preferably a fixed-frequency oscillator, which simplifies and reduces the costs of the test system. In particular, the oscillator 62 is chosen from among a dielectric resonator oscillator (DRO), in particular a ceramic dielectric resonator oscillator.

Such a resonator is for example marketed by the company General Electronic Devices, San Marcos, Calif., USA, under the name DRO. These resonators are in particular used in microwave oscillators, due to their robustness, low cost, and small size. They have very good phase stability typically expressed by a single-sideband phase noise (SSB phase noise) of less than −60 dBc/Hz at a frequency offset of 10 Hz.

The receiver 26 comprises a reception antenna 64 capable of measuring a signal received from the surface 12 on a bandwidth that does not need to exceed $10^{-8}$ times the transmission frequency.

In this way, the reception antenna 64 can receive the reflected signal 66 at a time-stable frequency, related to the average impedance of the surface 12 over the entire area lit by the transmission signal 24, and a signal 68 related to the radioelectric or geometric discontinuities caused by the defects 14 that affect the surface impedance.

The reflected signal 66 is generally received at the same frequency as the transmission frequency $F_e$ of the transmission signal 24.

The signal 68 connected to the radioelectric discontinuities is characterized by amplitude fluctuations and a frequency shift due to the relative rate of closure $V_r$ of the device 10 relative to the defects 14.

This rate of closure $V_r$ is equal to the tangential speed of travel V of the device 10 along the surface 12, multiplied by the cosine of the angle φ formed between the propagation direction of the signal 68 and the local tangent to the surface 12.

In light of the small height Δh, the angle φ is generally less than 45°, which makes it possible to increase the closure rate $V_r$.

In this way, the reception antenna 64 can receive a shifted frequency component of the transmission frequency representative of the Doppler shift between the transmission frequency $F_e$ and the reception frequency $F_r$.

This Doppler shift is generally given by the difference $F_r - F_e$ between the reception frequency and the transmission frequency and may be approached using the equation:

$$F_r - F_e = 2 V_r F_e / c \quad (2),$$

where c is the propagation rate of the electromagnetic radiation in the vacuum.

Furthermore, the antennas 60, 64 are housed in the central passage 48 and the cavity 42 to confine both the fields transmitted by the transmission antenna 60 and the field reflected on the surface 12 in the cavity 42. This is obtained by means of the conductive wall 40 forming a Faraday cage and by the absorbent shield 47.

Typically, the maximum propagation distance of the transmitted fields is less than 5 times the wavelength of the transmitted signal.

The control unit 30 can drive the oscillator 62 to transmit a transmission signal at the transmission frequency $F_e$. The control unit 30 can collect the signal received by the reception antenna 64 and transmit it to the extraction unit 34.

As specified above, the extraction unit 34 can extract, in the signal received by the receiver 26, a shifted frequency component of the transmission frequency $F_e$ resulting from a local impedance variation of the measured surface 12.

In particular, the extraction unit 34 is designed to extract a signal representative of the Doppler shift between the transmission frequency $F_e$ and the reception frequency $F_r$ when the device 10 is moved tangentially relative to the surface 12.

In one advantageous embodiment, shown in FIG. 2, the extraction assembly 34 comprises a heterodyne component capable of mixing frequencies between the signal received by the receiver 62 and the signal transmitted by the transmitter 22.

In the examples illustrated in FIG. 2, the extraction unit 34 comprises a blender 70, capable of blending the received signal with a portion of the transmission signal, and creating a beat signal at the shifted frequency component $F_r - F_e$ representative of the Doppler shift.

The extraction unit 34 also comprises a filter 72 capable of eliminating the component from the transmission frequency $F_e$ coming from the average measured impedance and eliminating the Doppler components coming from a shift of the transmitter 22 and the receiver 26 in a direction perpendicular to the surface 12.

This makes it possible to create an extracted signal representative of the shifted frequency component, corresponding to the Doppler shift between the transmission frequency and the reception frequency, at the tangential rate of closure $V_r$ of the device 10 on the surface.

Advantageously, the extraction unit 34 also comprises an output amplifier 74 capable of adapting the extracted signal in terms of level and impedance to distribute it to the display unit 36 in the form of an extracted signal representative of a local impedance variation of the surface.

In reference to FIG. 2, the blender 70 comprises a mixer 80 receiving at least part of the received signal $S_r(t) = A_r \cdot \cos(2\pi \cdot F_r \cdot t)$ to mix it with part of the transmission signal $S_e(t) = A_e \cdot \cos(2\pi \cdot F_e \cdot t)$, and at least one nonlinear component 82 capable of creating quadratic terms generating a low-frequency beat proportional to the Doppler shift $F_e - F_r$.

The mixer 80 is capable of creating a combined signal comprising the sum of the terms $S_r(t)$ and $S_e(t)$.

The nonlinear component 82 is for example a diode. It is capable of revealing quadratic terms generating a low-frequency beat proportional to $A_r \cdot A_e \cdot \cos[2\pi \cdot (F_r - F_e) \cdot t]$ that are included in the output signal.

The filter 72 is advantageously a filter that has a first low cutoff frequency F1, illustrated by FIG. 8. The frequency F1 corresponds to a Doppler shift at a minimum speed of travel. The speed $V_{min}$ is for example comprised between 5 mm/s and 20 cm/s. The low cutoff frequency is calculated using the following equation:

$$F1 = 2 \times V_{min} \times F_e / c.$$

The filter 72 has a second high cutoff frequency F2, capable of eliminating the carrier transmission frequency Fe and any parasitic transmission sources from the environment. To that end, the high frequency is chosen as a function of a maximum speed of travel $V_{max}$ and is calculated using the equation $F2 = 2 \times V_{max} \times F_e / c$.

The filter 72 is thus able to isolate the extracted signal representative of the shifted frequency component corresponding to the Doppler shift between the transmission frequency and the reception frequency, at the speed of travel of the device 10 on the surface.

The amplifier 74 can process the filtered signal from the filter 72 to adapt it in terms of level and impedance, so as to distribute it unaltered to the display unit 36. Advantageously, the signal produced as output from the amplifier 74, which corresponds to the signal extracted by the unit 34, is a so-called intermediate zero or "Fi0" or "baseband" frequency.

In the example illustrated in FIG. 2, the processing and display unit 36 comprises an enclosure detection assembly 90 of the extracted signal coming from the unit 34 and a display 92.

In this example, the enclosure detection assembly 90 comprises a rectifier 94 and an integrator 96 designed to stabilize the display and avoid overly brief alerts.

The display 92 comprises an intensity level indicator. This indicator may be a galvanometer, as illustrated by FIG. 2, or any other display system, such as a light-emitting diode system 97, as illustrated in FIG. 1.

In one alternative shown in dotted lines in FIG. 1, the display assembly 36 is detached relative to the holder 10. It is connected to the holder by a transmission means for transmitting the signal 100 that may include digitization means, such as a converter, and transmission means toward a monitor 101 connected to a computer.

The operation of the device 10 in the context of detecting defects 14 on a surface 12 will now be described.

Initially, the device 10 is positioned in contact with the surface 12 to be tested. To that end, the contact members 50 are placed on the surface 12. The cavity 42 then opens by means of the opening 46 across from a region 110 of the surface.

The space situated under the transmitter 22 and under the receiver 26 across from the surface 12 is completely free. The height ΔH separating the transmitter 22 and the receiver 26 from the surface 12 is smaller than the transmission wavelength, and in particular comprised between 6 mm and 1.5 mm.

Then, the device 10 is electrically powered, for example by a battery supported by the holder 20 or by an outside electricity source. The transmitter 22 is then activated.

The oscillator 62 creates a transmission signal at a transmission frequency $F_e$ comprised between 2 GHz and 80 GHz.

When the device 10 remains immobile on the surface, the transmission signal 24 reflects on the surface 12 and forms a received signal 28 that corresponds to the time-stable reflection 66 related to the average impedance of the surface over the entire lit area.

Figure 4:
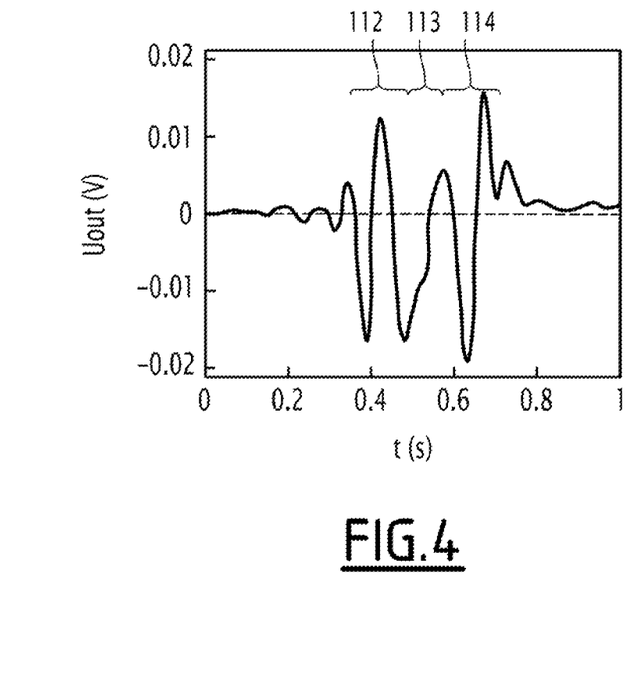
FIG. 4 illustrates a first example of the display of the signal produced by the device of FIG. 1, during passage over a surface defect.

The received signal 28 therefore does not create components characteristic of a surface impedance variation and is filtered by the cutoff frequency F2 of the filter 72. As illustrated by FIG. 4, the extracted signal is then substantially constant and equal to 0.

Then, the device 10 is moved tangentially relative to the surface 12, by sliding the bearing members 50 along the surface 12. The movement is done at a speed V generally comprised between 1 cm/s and 30 cm/s.

During this movement, when the surface 12 does not have any significant impedance defect and the transmitter 22 remains at a substantially constant height relative to the surface 12, the received signal remains representative of the stable reflection on the surface. The signal is therefore limited by the filter 72, and therefore does not create any variation in the extraction signal at the output of the unit 34.

Furthermore, if small height variations between the surface 12 of the transmitter 22 occur, in particular due to a curve variation of the surface 12, a Doppler component resulting from these variations may be created. The Doppler component is eliminated by the filter 72, in particular because it is at a lower frequency than the cutoff frequency.

Then, when the space situated below the cavity 42 is located in the vicinity of the defect 14, for example including a crack, a reflected signal 68 appears with a low angle of attack, in particular less than 45°.

The signal creates a Doppler frequency component once the defect 14 penetrates the test area delimited under the cavity 42.

As illustrated by the phase 112 and FIG. 4, the extracted signal then oscillates greatly at a frequency $F_r-F_e$, characterizing the Doppler shift observed at the rate of closure $V_r$.

Then, during the phase 113, the transmitter 22 passes across from the defect 14. Since the defect 14 is located just below the antenna 60, the rate of closure $V_r$ between the defect 14 and the antenna 60 decreases, given the angle of attack during the phase 113, which becomes close to $\pi/2$.

The frequency of the extracted signal then becomes less than 5 Hz, which is the cutoff frequency chosen for the filter 72.

Then, during the phase 114, when the transmitter 22 passes beyond the defect 14, the extracted signal again oscillates greatly, at the oscillation frequency $F_r-F_e$ corresponding to the observed Doppler shift.

The signal extracted by the unit 34 can then be transmitted to the display unit 36 to be displayed either in the form of a continuous variation of a level indicator, for example represented by a galvanic meter, or by a discrete variation of an indicator, such as a set of diodes.

Alternatively, the extracted signal is transmitted to an external display unit 36, for example a computer, and is displayed directly on a monitor 101.

The device 10 according to the invention is very sensitive to local surface impedance variations, which makes it possible to detect small defects, which may even be invisible to the naked eye on a surface 12. In particular, small metallization defects not visible to the naked eye in a conductive surface, and small radioelectric transparency defects on a dielectric surface, are detectable using the device 10 according to the invention.

As an example, it is possible to detect scratches with a length smaller than 2 mm and a width smaller than 1 micrometer present in a metallization layer. It is also possible to detect transparency defects related to a wire 1 mm long with a diameter smaller than 10μ in a dielectric wall.

The measurement done by the device 10 is not particularly sensitive to the test environment. Thus, even if reflective elements are present in the vicinity of the device 10, the measurement is not disrupted, which makes it possible to use it on-site, without requiring specific preparation.

The device 10 is also extremely compact, and may be grasped and moved by a user's hand.

It for example has a size comparable to that of a computer mouse or cellular telephone. Furthermore, the device 10 is completely autonomous and does not require an improved computer to exploit the measured signals, unlike the radar measurement techniques.

The device 10 thus makes it possible to scan a surface continuously by sliding the sensor on the surface, in particular by manual movement.

The device 10 according to the invention performs particularly well to qualify the homogeneity of the electromagnetic characteristics of a surface for frequency wavelengths greater than 300 MHz. This makes it possible to test walls whereof the radioelectric function is to reflect, focus, or disperse the electromagnetic rays.

In one alternative, the signal extracted by the extraction unit 34, advantageously digitized, can be sent to a computer 102. The computer 102 can display its evolution as a function of time as shown in FIG. 4. Furthermore, the computer 102 can calibrate the measured level of the impedance discontinuity 14 and deduce therefrom, using a calibration process using one or more target standards, a measurement in terms of equivalent radar surface (ERS) for each impedance discontinuity on the surface 12.

The device 10 according to the invention can detect equivalent radar surfaces of only $10^{-9}$ m$^2$, using a very simple embodiment, for example when it operates at a frequency close to 10 GHz.

Figure 5:
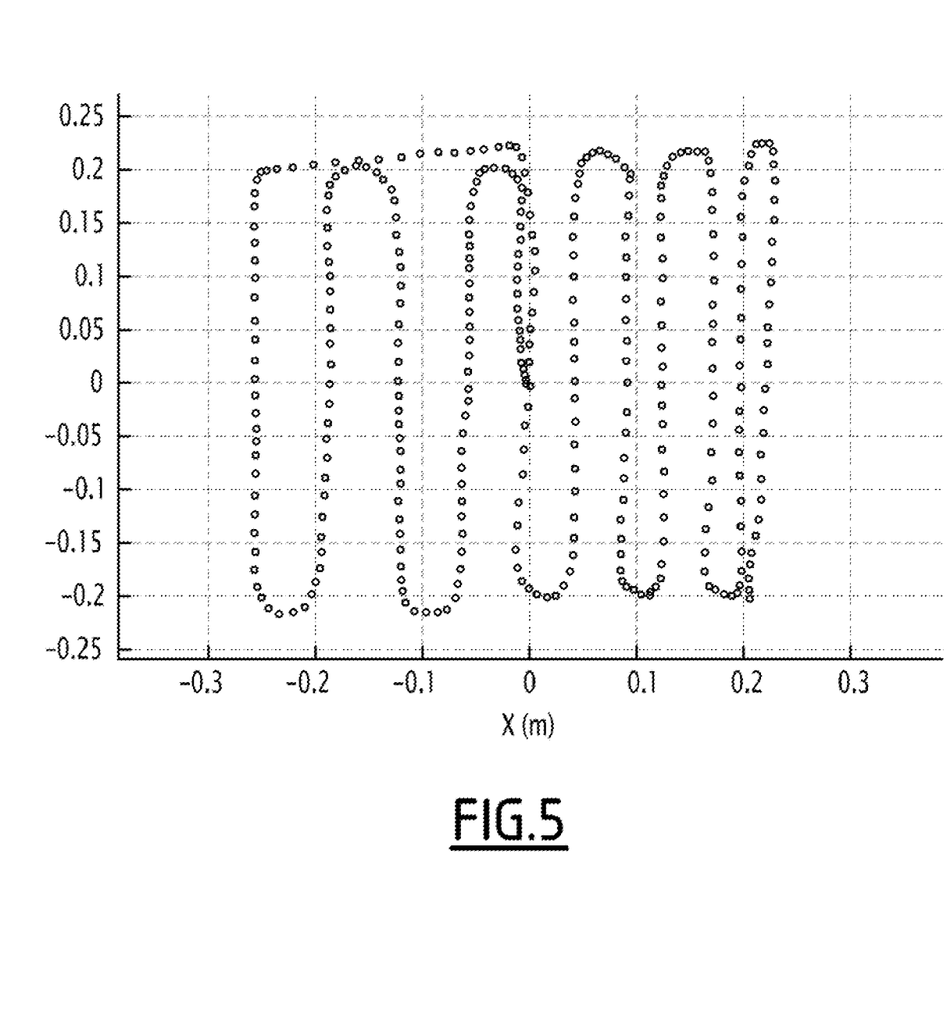
FIG. 5 is a view similar to FIG. 4 during spatial scanning of a given surface.

In another alternative, a position sensor 201 is integrated into the device 10. The sensor 201 can be moved jointly with the holder 20. The unit 30 is then capable of recording the intensity of the signal extracted by the extraction unit 34 as a function of the position detected by the position sensor 201, and producing maps of impedance discontinuities on a surface, as shown in FIG. 5. This makes it possible to have an overall view that localizes and compares the levels of the impedance discontinuities.

In one advantageous alternative, the speed of movement of the device 10 on the holder 12 is also measured using data from the position sensor 201, or using a separate acceleration sensor to correct the observed signal as a function of the speed variations that affect the intensity received through the spectral response of the filter 72. In that case, a calibration may be done to determine an absolute reflectivity value over a wide speed range.

In still another alternative, the guide assembly 21 comprises rolling members, such as wheels.

In that case, it is necessary to make the radioelectric properties of the wheels radially uniform to avoid creating a Doppler component coming from the reflection of the waves transmitted by the transmitter 22 on the moving elements of the rolling members relative to the antennas 60, 64.

In still another alternative, the guide member 21 can move the device 10 parallel to the surface 12, without placing the device 10 in contact with the surface 12. This movement is for example done by a robot that performs mechanical guiding and precisely monitors the distance separating the transmitter 22 and the receiver 26 from the surface 12 to ensure a reproducible measurement in terms of speed and separation.

Thanks to the availability of the inner cavity 42, delimited upward and at its periphery by the metal wall 44 of the hollow housing 40, the field transmitted by the transmission antenna 60 and the field reflected on the surface 12 are confined in the cavity 42, the cavity 42 opening exclusively through the lower opening 46 placed across from the surface 12.

It is thus possible to detect very weak signals of interest which are produced by interaction of the transmitted electromagnetic wave with the smallest defects of the tested surface 12, by separating the signals of interest from those of the test environment, while still having a low speed of travel on the surface 12.

The low speed of travel produces a Doppler shift, for example lower than 100 Hz, even lower than 50 Hz, for example in the order of several Hz.

This goes against the known Doppler detections, which are usually carried out with a high speed of travel, to separate the signal of interest from the Doppler components resulting from the environment. The known Doppler detections need a large space to allow the travels of the device, and have a limited sensitivity to detect small defects.

In the apparatus 10 according to the invention, the Doppler detection which is carried out is sensitive to the modifications of the signal which is diffused through the opening 46 of the hollow housing 40. This detection mode is unsensitive to reflections which are external to the region of the surface 12 which is located across the opening 46 provided for detecting the small defects.

In other respects, the detection mode of the invention produces Doppler components which result from the appearance speed of a defect in the opening 46 of the housing 40. The progressive unmasking of the defect modifies the signal which is detected by the extraction unit 34.

The device 10 according to the invention is particularly efficient, due to the use of a low phase-noise oscillator such as a dielectric resonator oscillator (DRO). Such an oscillator provides an appropriate sensitivity, even if the travel of the device 10 on the surface 12 is small, and is made at low speed, hence producing Doppler frequencies of a few Hz, representing for example a billionth of the transmission frequency.

While the foregoing is directed to embodiments of the present invention, other and further embodiments of the invention may be devised without departing from the basic scope thereof, and the scope thereof is determined by the claims that follow.

The invention claimed is:

1. A device for testing a surface, comprising:
a holder;
a transmitter supported by the holder, the transmitter being able to transmit an electromagnetic signal to the surface at a transmission frequency (Fe);
a receiver for receiving a signal reflected on the surface; and
a guide assembly for the holder to move the transmitter and the receiver across from the surface, tangentially relative to the surface, the device comprising an extraction unit for extracting a shifted frequency component (Fr-Fe) of the transmission frequency (Fe) resulting from a local impedance variation of the surface in the signal received by the receiver, the extraction unit producing an extracted signal that is representative of a state of the surface from the shifted frequency component,
wherein the guide assembly comprises at least one skid and/or a rolling member capable of keeping the transmitter and the receiver at a substantially constant distance across from the surface, during the tangential movement of the holder on the surface.

2. The device according to claim 1, wherein that the shifted frequency component is representative of a Doppler shift between the transmission frequency and a reception frequency of the signal received by the receiver at a speed of travel of the device on the surface.

3. The device according to claim 1, wherein the extraction unit comprises a mixer for mixing at least part of the signal received by the receiver with at least part of the transmission signal transmitted by the transmitter and a nonlinear component capable of producing a processed signal comprising an oscillation at the shifted frequency component based on the combined signal obtained in the mixer.

4. The device according to claim 3, wherein the extraction unit comprises a frequency filter capable of eliminating the frequencies below a minimum cutoff frequency, advantageously equal to 2 Vmin Fe/c, where Vmin is a lower bound of the speed of movement of the device on the surface, Fe is the transmission frequency, and c is the speed of the electromagnetic radiation in the vacuum, the frequency filter being capable of eliminating frequencies above an upper cutoff frequency, in particular equal to 2 Vmax Fe/c where Vmax is an upper bound of the speed of movement of the device on the surface.

5. The device according to claim 1, further comprising a display unit capable of displaying a variable intensity signal as a function of the state of the surface, the variable intensity signal being produced from the signal extracted in the extraction unit.

6. The device according to claim 5, wherein the display unit comprises a processing assembly for processing the extracted signal obtained as output from the extraction unit, the processing assembly comprising an enclosure detector comprising a rectifier and an integrator.

7. The device according to claim 1, further comprising an analog-digital converter capable of digitizing the extracted signal from the extraction unit.

8. The device according to claim 1, further comprising a detection sensor for detecting the position of the device on the surface, the device advantageously comprising an assembly for storing the extracted signal obtained by the extraction unit as a function of the position of the device on the surface.

9. The device according to claim 1, wherein the holder is portable to be grasped in a user's hand.

10. The device according to claim 1, wherein the holder comprises a conductive wall delimiting a cavity, the transmitter and the receiver being received in the cavity.

11. The device according to claim 10, wherein the conductive wall delimits a lower opening through which the cavity opens, the lower opening being designed to be positioned across from the surface.

12. The device according to claim 10, wherein the holder comprises at least one shield made from a material absorbing the electromagnetic waves at the transmission frequency (Fe), the shield being positioned in the cavity delimited by the conductive wall, across from the transmitter and the receiver.

13. The device according to claim 1, wherein the guide assembly comprises a guide mechanism driven from the holder across from the surface, advantageously keeping the device separated from the surface.

14. A method for testing a surface, the method comprising the following steps:
   providing a device as recited in claim 1;
   tangential movement of the holder across from the surface by means of the guide assembly;
   transmission of an electromagnetic signal at a transmission frequency (Fe) by the transmitter;
   reception of a reflected signal on the surface by the receiver;
   extraction, by the extraction unit, of a shifted frequency component of the transmission frequency in the signal received by the receiver, the shifted frequency component resulting from a local impedance variation of the surface; and
   production of an extracted signal representative of a state of the surface from the extracted frequency component.

15. The method according to claim 14, wherein the extraction step comprises mixing at least part of the reception signal received by the receiver with at least part of the transmission signal transmitted by the transmitter to form a combined signal, and the application of the combined signal to a non-linear component to produce an oscillating extracted signal at the shifted frequency component.

16. A device for testing a surface, comprising:
a holder;
a transmitter supported by the holder, the transmitter being able to transmit an electromagnetic signal to the surface at a transmission frequency (Fe);
a receiver for receiving a signal reflected on the surface; and
a guide assembly for the holder to move the transmitter and the receiver across from the surface, tangentially relative to the surface, the device comprising an extraction unit for extracting a shifted frequency component (Fr-Fe) of the transmission frequency (Fe) resulting from a local impedance variation of the surface in the signal received by the receiver, the extraction unit producing an extracted signal that is representative of a state of the surface from the shifted frequency component,
wherein that the shifted frequency component is representative of a Doppler shift between the transmission frequency and a reception frequency of the signal received by the receiver at a speed of travel of the device on the surface,
wherein the holder comprises a conductive wall delimiting a cavity, the transmitter and the receiver being received in the cavity,
wherein the conductive wall delimits a lower opening through which the cavity opens, the lower opening being designed to be positioned across from the surface,
wherein the holder comprises at least one shield made from a material absorbing the electromagnetic waves at the transmission frequency (Fe), the shield being positioned in the cavity delimited by the conductive wall, across from the transmitter and the receiver.

\* \* \* \* \*